United States Patent [19]

Makuuchi et al.

[11] Patent Number: 6,117,815
[45] Date of Patent: Sep. 12, 2000

[54] PLANT GROWTH PROMOTER

[75] Inventors: Keizo Makuuchi; Fumio Yoshii; Naotsugu Nagasawa; Tamikazu Kume; Quoc Hien Nguyen, all of Gunma-ken, Japan

[73] Assignee: Agency of Industrial Science and Technology, Japan Atomic Energy Research Institute, Japan

[21] Appl. No.: 09/166,549

[22] Filed: Oct. 5, 1998

[30] Foreign Application Priority Data

Oct. 8, 1997 [JP] Japan ............................ 9-275890

[51] Int. Cl.⁷ .......................... A01N 43/16; A01N 65/00; A01N 61/00
[52] U.S. Cl. .......................... 504/116; 504/118; 504/140; 504/292; 71/DIG. 1
[58] Field of Search ........................ 424/195.1; 514/54; 504/116, 118, 140, 292; 71/DIG. 1

[56] References Cited

U.S. PATENT DOCUMENTS

| 3,336,129 | 8/1967 | Herrett et al. | 504/116 |
| 3,900,378 | 8/1975 | Yen et al. | 504/326 |
| 4,993,185 | 2/1991 | Adachi et al. | 47/58.1 |
| 5,588,254 | 12/1996 | Adachi et al. | 47/57.6 |

OTHER PUBLICATIONS

Kume, T. et al., "Effect of Gamma–irradiation on Sodium Alginate and Carrageenan Powder," Agric. Biol. Chem., vol. 47 (4), pp. 889–890, 1993.

*Primary Examiner*—John Pak
*Attorney, Agent, or Firm*—Banner & Witcoff, Ltd.

[57] ABSTRACT

Sodium alginate which is an oceanic natural resource is exposed, either in aqueous solution or in a dry state, to a radiation so that it is decomposed to a lower-molecular weight polysaccharide, which is processed into a dilute aqueous solution that is either used as a hydroponic solution or foliar spraying so as to promote their growth.

8 Claims, No Drawings

PLANT GROWTH PROMOTER

BACKGROUND OF THE INVENTION

This invention relates to an inexpensive and safe plant growth promoter. The populations of developing countries are increasing in an explosive manner and a need exists for increasing food production. However, several reasons including the devastation of arable land, desertification and the decrease in crop lands due to industrialization, developing countries are having very hard times in producing more food and have felt a strong need to develop an effective plant growth promoter. The present invention enables a safe and inexpensive plant growth promoter to be produced from oceanic natural resources and holds much promise for a future increase in food production.

Polysaccharides such as chitin and chitosan are known to increase the harvest of vegetables. The product of enzymatic decomposition of sodium alginate has been proposed for use as a plant growth promoter. However, the method of decomposing sodium alginate with enzymes is costly and it has been desired to develop a method by which sodium alginate can be decomposed at a lower cost but in a safe and effective way.

SUMMARY OF THE INVENTION

It is, therefore, an object of the present invention to provide a safe and inexpensive plant growth promoter from sodium alginate which is an oceanic natural resource.

In the course of their studies on decomposing or crosslinking water-soluble polymers by exposure to radiations, the present inventors found that polysaccharides obtained by exposure to radiations had a marked plant growth promoting effect. The present inventors continued their studies with a view to finding a practical application for this finding and have eventually accomplished the present invention.

In the present invention, sodium alginate which is an oceanic natural resource is decomposed either in aqueous solution or in a dry state to produce a low-molecular weight polysaccharide which, when used as a dilute aqueous solution in hydroponics or foliar spraying in soil, has been found to exhibit a marked plant growth promoting effect.

Thus, in accordance with the present invention, sodium alginate in the form of either an aqueous solution or a powder is exposed to a radiation made of γ-rays or electron beams at a dose of 10–500 kGy, whereupon the sodium alginate is decomposed to produce a low-molecular weight polysaccharide useful as a plant growth promoter which, when dissolved in water to make a dilute aqueous solution, can suitably be used in hydroponic cultivation of plants or sprayed over plant leaves, thereby promoting the growth of the plants.

DETAILED DESCRIPTION OF THE INVENTION

The present invention relates to a plant growth promoter produced by radiation-induced decomposition of an oceanic natural resource sodium alginate either in solution or in a dry state. Sodium alginate as used in the invention is one of the polysaccharides contained in sea weeds; it occurs as a material that composes the cell walls of the weeds and that fill the intracellular spaces; briefly, it is a triuronic acid mixture composed of D-mannuronic acid and L-guluronic acid. Oceanic polysaccharides such as chitin, chitosan and caragheenin may also be decomposed by radiations to produce the plant growth promoter of the invention.

Radiation sources that may be employed in the invention are $^{60}$Co and an electron beam accelerator. Irradiation with γ-rays from $^{60}$Co can be performed by various known methods. The electron beam accelerator to be used may be a low-energy electron beam accelerator of the type described in Japanese Patent Public Disclosure No. 73609/1997 (Japanese Patent Application No. 211461/1994). Medium- and high-energy electron beam accelerators may also be used.

The dose of radiations to be applied in the invention ranges from 10 to 500 kGy depending upon the concentration and state of sodium alginate to be irradiated. Sodium alginate in a powder form (in a dry state) requires greater doses but need be irradiated in smaller volumes than when it is in aqueous solution. In irradiation of the aqueous solution, the dose to achieve the same degree of decomposition increases with the increasing concentration of sodium alginate. The dose of 10 kGy is a minimal value for obtaining the desired plant growth promoter. The dose of 500 kGy is required for decomposing sodium alginate in a water-free dry state by radiation.

Specifically, a powder of sodium alginate having a molecular weight of ca. 420,000 produces a decomposed polysaccharide of a molecular weight of ca. 170,000 if it is irradiated to a total dose of 10 kGy. A decomposed polysaccharide having a molecular weight of ca. 9,000 results if the dose is increased to 500 kGy. An aqueous solution of sodium alginate having a molecular weight of ca. 420,000 produces a decomposed polysaccharide of a molecular weight of ca. 40,000 if it is irradiated to a total dose of 10 kGy. A decomposed polysaccharide having a molecular weight of ca. 6,400 results if the dose is increased to 100 kGy.

One of the characteristic features of the invention is to irradiate sodium alginate in aqueous solution but no special procedure is necessary to prepare an aqueous solution of sodium alginate and any conventional methods may be adopted.

The following examples and comparative examples are provided to further illustrate the present invention. It should be noted that sodium alginate which is a natural substance may have varying properties depending upon the place of seaweed growth, as well as in what season seaweed is harvested, and the method by which alginate is extracted. Hence, the essential significance of the invention will in no way be impaired by slight differences in physical properties of sodium alginate from those set forth in the following examples and comparative examples.

EXAMPLE 1

Four grams of a purchased powder of sodium alginate was dissolved in water to give a concentration of 4%. After allowing the sodium alginate to swell at room temperature, the mixture was stirred with a magnetic stirrer to form an aqueous solution. The prepared aqueous solution was divided in 20-cc portions which were transferred into five test tubes, which were closed with rubber stoppers and irradiated with γ-rays at an hourly dose rate of 10 kGy to give total doses of 0, 20, 50, 100, and 200 kGy.

The irradiated aqueous solutions were added to hydroponic solution at a concentration of 20 ppm and used for the cultivation of rice. A 2000-fold dilution of Hyponex for vegetables (N:P:K=8:12:6) was used as a fertilizer in hydroponics. Ten days after the start of culture, seedlings with the root were collected from the respective test culture backers and their dry matters were measured. The results are shown in Table 1, in which the "percent weight increase" is referenced to the weight of rice that was subjected to hydroponics without sodium alginate. This definition applies to the following examples and comparative examples.

Comparative Example 1

Rice was cultivated as in Example 1, except that the hydroponic solution did not contain sodium alginate. The result is also shown in Table 1.

TABLE 1

|  | Ex. 1 | Ex. 1 | Ex. 1 | Ex. 1 | Comp. Ex. 1 | Comp. Ex. 2 | Ex. 2 |
|---|---|---|---|---|---|---|---|
| Concentration of sodium alginate in hydroponic solution, ppm | 20 | 20 | 20 | 20 | 0 | 20 | 20 |
| Dose kGy | 20 | 50 | 100 | 200 | 0 | 0 | 500 |
| Dry weight | 184 | 190 | 201 | 198 | 166 | 175 | 200 |
| Percent weight increase | 10.8 | 14.5 | 21.1 | 19.3 | 0 | 5.4 | 19.5 |

Comparative Example 2

Rice was cultivated as in Example 1, except that the hydroponic solution contained 20 ppm of unirradiated sodium alginate. The result is also shown in Table. 1.

As one can see from the data shown in Table 1, an effective plant growth promoter can be produced by exposing an aqueous solution of sodium alginate to radiation. It is also clear from Table 1 that the total dose of radiation must be more than 10 kGy in order to achieve crop yield or dry matter increases higher than 10%.

EXAMPLE 2

A sodium alginate powder of the same type as used in Example 1 was transferred into a test tube which was closed with a rubber stopper. After irradiating the powder with γ-rays to a total dose of 500 kGy at a dose rate of 10 kGy/h, the powder was dissolved in hydroponic solution as mentioned above at a concentration of 20 ppm. The prepared aqueous solution was used for cultivation of rice. The result is shown in Table 1.

Example 2 shows that an effective plant growth promoter can also be produced by exposing a powder of sodium alginate to a radiation.

EXAMPLE 3

In this example, the effect of the concentration of radiation decomposed sodium alginate on the crop yield of hydroponically cultivated rice was investigated. To this end, a 4% aqueous solution of sodium alginate was irradiated with 100 kGy of γ-rays and diluted to concentrations of 10, 20, 50 and 100 ppm in hydroponic solution as mentioned above. The results of hydroponic cultivation of rice in these solutions are shown in Table 2. A maximum rice crop yield was achieved from the 50-ppm solution.

Comparative Example 3

The result of hydroponic cultivation of rice without sodium alginate is shown in Table 2. Obviously, the percent weight increase of rice was zero.

TABLE 2

|  | Ex. 3 | Ex. 3 | Ex. 3 | Ex. 3 | Comp. Ex. 3 |
|---|---|---|---|---|---|
| Concentration of irradiated sodium alginate in hydroponic solution, ppm | 10 | 20 | 50 | 100 | 0 |
| Percent weight increase of rice | 10.6 | 20.7 | 23.3 | 17.3 | 0 |

EXAMPLE 4

In this example, the effect of the concentration of radiation decomposed sodium alginate on the crop yield of hydroponically cultivated peanut was investigated. Nutrient Solution of Hyponex (1/1000) was applied weekly. To this end, a 4% aqueous solution of sodium alginate was irradiated with 100 kGy of γ-rays and diluted to concentrations of 10, 50, 100 and 200 ppm and used as foliar spray on peanut leaves. The results of dry matter of peanut are shown in Table 3. A maximum crop yield of peanut was achieved from the 100-ppm treatment.

Comparative Example 4

The result of crop yield of peanut without a sodium alginate is shown in Table 3. Obviously, the percent weight increase of peanut was zero.

TABLE 3

|  | Ex. 4 | Ex. 4 | Ex. 4 | Ex. 4 | Comp. Ex. 4 |
|---|---|---|---|---|---|
| Concentration of irradiated sodium alginate in hydroponic solution, ppm | 10 | 50 | 100 | 200 | 0 |
| Percent weight increase of peanut | 28.4 | 40.0 | 60.0 | 7.7 | 0 |

According to the present invention, a safe and inexpensive plant growth promoter useful for achieving increased food production in developing countries can be produced using an oceanic natural resource sodium alginate as a starting material. Briefly, the plant growth promoter is produced by decomposing sodium alginate through irradiation. The molecular weight of the decomposition product can easily be adjusted by controlling the dose of radiation and, hence, the degree of its decomposition can be selected at appropriate levels. This offers one great advantage for the present invention, that is its the ability to perform the radiation-decomposition of sodium alginate in a safe, effective and consistent manner.

In addition, sodium alginate can be irradiated whether it is in aqueous solution or in a powder state. The plant growth promoter obtained is suitable to add into hydroponic solution or to use as foliar spray or to disperse in soil.

What is claimed is:

1. A method for promoting plant growth comprising exposing an aqueous solution of sodium alginate or a powder of sodium alginate to 10–500 kGy of γ-rays or electron beams to obtain a radiation-induced decomposition product of sodium alginate, diluting the decomposition product in water to obtain a hydroponic solution, and applying the hydroponic solution to a plant in an effective amount to promote growth of the plant.

2. The method of claim 1 wherein the aqueous solution of sodium alginate or a powder of sodium alginate is exposed to γ-rays.

3. The method of claim 1 wherein the aqueous solution of sodium alginate or a powder of sodium alginate is exposed to electron beams.

4. The method of claim 1 wherein the decomposition product is diluted in water to obtain a hydroponic solution containing 10–100 ppm of the decomposition product.

5. A method for growing plants comprising exposing an aqueous solution of sodium alginate or a powder of sodium alginate to 10–500 kGy of γ-rays or electron beams to obtain a radiation-induced decomposition product of sodium alginate, diluting the decomposition product in water to obtain a hydroponic solution, and growing a plant in the hydroponic solution.

6. The method of claim 5 wherein the aqueous solution of sodium alginate or a powder of sodium alginate is exposed to γ-rays.

7. The method of claim 5 wherein the aqueous solution of sodium alginate or a powder of sodium alginate is exposed to electron beams.

8. The method of claim 5 wherein the decomposition product is diluted in water to obtain a hydroponic solution containing 10–100 ppm of the decomposition product.

* * * * *

UNITED STATES PATENT AND TRADEMARK OFFICE
CERTIFICATE OF CORRECTION

PATENT NO.: 6,117,815
DATED: September 12, 2000
INVENTORS: Keizo MAKUUCHI, *et al.*

It is certified that an error appears in the above-identified patent and that said Letters Patent is hereby corrected as shown below:

On the cover page, in the Assignee information [73], "Agency of Industrial Science and Technology" has been deleted.

Signed and Sealed this

First Day of May, 2001

*Attest:*

NICHOLAS P. GODICI

*Attesting Officer*  *Acting Director of the United States Patent and Trademark Office*